United States Patent [19]
Warneck et al.

[11] Patent Number: 5,912,164
[45] Date of Patent: Jun. 15, 1999

[54] STEREOSELECTIVE HYDROLYSIS OF CHIRAL CARBOXYLIC ACID ESTERS USING ESTERASE FROM OPHIOSTOMA OR CERATOCYSTIS

[75] Inventors: Julie Belinda Hazel Warneck, Huntingdon; Richard Anthony Wisdom, Histon, both of United Kingdom

[73] Assignees: Laboratorios Menarini S.A., Badalona, Spain; Chirotech Technology Limited, Cambridge, United Kingdom

[21] Appl. No.: 08/854,097

[22] Filed: May 9, 1997

Related U.S. Application Data

[63] Continuation-in-part of application No. 08/530,261, Aug. 31, 1995, abandoned, and a continuation-in-part of application No. 08/513,753, Sep. 5, 1995, abandoned.

[30] Foreign Application Priority Data

| Mar. 3, 1993 | [GB] | United Kingdom | 9304256 |
| Mar. 3, 1993 | [GB] | United Kingdom | 9304351 |
| Mar. 3, 1994 | [WO] | WIPO | PCT/GB94/00408 |
| Mar. 3, 1994 | [WO] | WIPO | PCT/EP94/00630 |

[51] Int. Cl.$^6$ .................. C12P 7/40; C07C 1/04
[52] U.S. Cl. .................. 435/280; 435/136; 435/911
[58] Field of Search ............... 435/280, 136, 435/911

[56] References Cited

U.S. PATENT DOCUMENTS

| 5,661,014 | 8/1997 | Evans et al. | 435/122 |
| 5,750,764 | 5/1998 | Marais et al. | 560/56 |

FOREIGN PATENT DOCUMENTS

| 0 227 078 | 7/1987 | European Pat. Off. |
| 0 233 656 | 8/1987 | European Pat. Off. |
| 0 407 033 | 1/1991 | European Pat. Off. |
| 0 195 717 | 10/1991 | European Pat. Off. |
| 93/04189 | 3/1993 | WIPO |
| 93/04190 | 3/1993 | WIPO |
| 93/23547 | 11/1993 | WIPO |
| 93/25703 | 12/1993 | WIPO |
| 93/25704 | 12/1993 | WIPO |

*Primary Examiner*—Sandra E. Saucier
*Attorney, Agent, or Firm*—Griffin, Butler, Whisenhunt & Szipl, LLP

[57] ABSTRACT

An organism of the genus Ophiostoma or Ceratocystis, or a material having enzymatic activity derived therefrom, is used as a stereo-specific agent, in a biotransformation reaction, for the production of an enantiomeric acid or alcohol from a mixture of enantiomers of an ester thereof.

14 Claims, No Drawings

STEREOSELECTIVE HYDROLYSIS OF CHIRAL CARBOXYLIC ACID ESTERS USING ESTERASE FROM OPHIOSTOMA OR CERATOCYSTIS

REFERENCE TO EARLIER APPLICATION

This Application is a continuation-in-part of applications Ser. No. 08/530,261, filed Aug. 31, 1995, now abandoned, and Ser. No. 08/513,753, filed Sep. 5, 1995, now abandoned.

FIELD OF THE INVENTION

This invention relates to biotransformation using an esterase.

BACKGROUND OF INVENTION

Many compounds are chiral, and it is often desirable to obtain a substantially pure enantiomer from the racemate that is usually available, by conventional chemical synthesis. Such chiral compounds include a number of 2-arylpropionic acids that are well known as anti-inflammatory agents. Examples include ibuprofen, naproxen and ketoprofen. It is now well established that the major therapeutic activity of each resides in the (S)-enantiomer.

Several methods for obtaining the (S)-enantiomer, free of contaminating (R)-enantiomer, are known. These include asymmetric chemical synthesis and chemical resolution such as the stoichiometric crystallisation of diastereomeric salts formed with various chiral amines.

An alternative approach is biocatalytic, using a biocatalyst to selectively hydrolyse an ester of the 2-arylpropionic acid. If a biocatalyst with the correct stereo-specificity can be identified, a reaction mixture containing the unreacted ester of one enantiomer plus the acid product of the other enantiomer can be obtained. Separation and recovery of the product are then relatively facile. Unreacted ester can be racemised and reused in a further reaction, thereby ensuring almost complete conversion of the racemic substrate to the required single enantiomer product.

EP-A-0227078 describes the use of several extracellular, commercially-available microbial lipases in such biocatalytic resolutions. In general, however, large amounts of enzyme were required and the reaction took 2-6 days. Such reactions would therefore be expensive to operate. The best enzyme powder identified was that from *Candida cylindraceae* (also known as *Candida ruposa*); however, in EP-A-0407033, it was shown that this preparation, as well as having low activity, contained more than one enzyme with esterase activity. Further, in order to obtain ketoprofen with a high ee (enantiomeric excess), it was necessary to purify the preparation.

EP-A-0233656 describes the isolation and cloning of an esterase gene from *Bacillus thai*. This enzyme is shown to selectively hydrolyse the ethyl and methyl esters of both naproxen and ibuprofen to give the (S)-acid of respective compounds. It is also shown that cloning of the enzyme resulted in a preparation giving a higher ee product, as a result of minimising other enzyme side-activities.

WO-A-9323547 describes a number of strains which also produce an esterase which selectively hydrolyses naproxen esters. The best strain found was *Zopfiella latipes*, the esterase from which had been cloned.

WO-A-9304189 describes an organism, Trichosporon sp, that is able to selectively hydrolyse the (S)-enantiomer of ethyl ketoprofen to give an (S)-acid product having an ee of >90%. The enzyme that carries out this biotransformation is intracellular. As stable cell-free preparations have proved difficult to obtain, it is difficult to increase biocatalytic activities by gene cloning or classical mutagenesis.

For economic biotransformation, it is important that cloning techniques should be available, to help reduce enzyme costs. In EP-A-0233656, the relative specific activity of the esterase in the wild Bacillus isolate was very low; thus, even after cloning and hyper-expression of the enzyme, biocatalyst costs are still likely to be significant.

An object behind the present invention has been to obtain a biocatalyst which has good activity against esters, which gives good ee acid product, and which would be suitable for cloning and hyper-expression, e.g. in *E. coli*, to enable biocatalyst costs to be kept to a minimum.

SUMMARY OF INVENTION

Surprisingly, a screen of microorganisms from a range of different sources showed that the ascomycete *Ophiostoma novo-ulmi* (also known as *Ceratocystis ulmi*) produced an intracellular hydrolytic enzyme having the desired activity. Further tests demonstrated that, unlike the strain disclosed in WO-A-9304189, stable cell-free activity could be obtained and that therefore it was suitable for cloning and potential use in cell-free biotransformations. *Ophiostoma novo-ulmi* is a plant pathogen known to be the virulent causative agent of Dutch Elm disease. It is known to be closely related to less virulent strains of *Ophiostoma ulmi* and also to *O. piceae*.

Following the primary discovery underlying the present invention, it has been found that stereo-specific esterase activity is present in alternative strains of *Ophiostoma novo-ulmi* in *Ophiostoma ulmi* (also sometimes known as *Ceratocystis ulmi*) and *Ophiostoma piceae* (also sometimes known as *Ceratocystis piceae*) and from isolates collected from various locations in the U.S.A., Europe, the Middle East and Uzbekistan. In addition, alternative strains of Ceratocystis sp. obtained from the IMI, Egham, Surrey, UK have been obtained and screened for activity. It has been discovered that the activity is also present in strains *C. coronata* (e.g. IMI 176533), *C. ips* (e.g. IMI 212114), *C. tetropii* (e.g. IMI 212117), *C. cainii* (e.g. IMI 176523), *C. arborea* (e.g. IMI 176529) and *C. stenoceras* (e.g. IMI 268494). The activity appears therefore to be widespread amongst a range of alternative Ceratocystis strains collected from different locations in the world.

A strain of the original isolate screened, herein described as AJ3, was deposited at the International Mycological Institute, Bakeham Lane, Egham, Surrey TW209TY, United Kingdom on 15th Feb. 1993, with the accession number IMI 356050, under the terms of the Budapest Treaty. This strain provides a good example of the stereo-specific activity; however, given the widespread nature of the activity in a wide variety of related strains, the scope of the invention is not intended to be limited to this particular organism. The invention also extends to the use of enzymatic activity isolated from such organisms, by any suitable technique. The enzyme per Se, or a fusion protein, including the active sequence, may for example be obtained.

BRIEF DESCRIPTION OF THE DRAWINGS

FIG. 1 is a restriction digest map of recombinant plasmids obtained in the cloning of the deposited organism having esterase activity.

DESCRIPTION OF THE INVENTION

In accordance with the present invention, microorganisms of the genus Ophiostoma and their enzymatic activity can be used to hydrolyse the racemic $C_{1-3}$ alkyl, e.g. ethyl ester of 2-arylalkanoic acids such as ketoprofen or naproxen stereoselectively, to yield the acid substantially enriched in the (S)-enantiomer, e.g. to 93–96% enantiomeric excess, or more, and leave residual ester enriched with the (R)-enantiomer.

Other substrates include compounds in which the alcohol function is chiral, e.g. esters of 2-methoxycyclo-hexanol with an alkanoic acid. The novel esterase is thus of wide applicability, although its efficacy on any given substrate can readily be determined by simple experiment. Depending on the nature of the substrate, the (R) or (S)-acid or alcohol may be produced, in admixture with the (S) or (R)-residual ester, respectively.

The reaction can be conducted on any mixture of enantiomers of the ester, although that mixture will usually be the racemate. The reaction is preferably conducted at pH 8–11, mote preferably 9.5–10.5, and most preferably about 10. A solvent, e.g. an organic solvent such as cyclohexane, may be employed.

Use of the biocatalyst described is beneficial for the production of chiral alcohols, acids or esters of high enantiomeric purity. Standard chemical procedures may be used to separate out the desired product and, where possible, to racemise for reuse the unwanted enantiomer. In the case where the acid or alcohol formed during the biotransformation has the desired stereochemistry, it is usual to stop the biotransformation at less than 50% conversion to ensure maximal enantiomeric purity of the hydrolytic products. In cases where the residual ester has the required stereochemistry, it is usual to proceed with the biotransformation to greater than 50%. Indeed, in cases where the ester substrate is such that the available biocatalysts have low enantiospecificity, it is generally desirable to select a biocatalyst which preferentially hydrolyses the ester with the incorrect stereochemistry, so leaving the residual ester as the desired product. In this way, it is possible to greatly increase the enantiomeric excess (ee) of the ester product by taking the biotransformation to greater than 50% conversion. Whilst such procedures are known to those skilled in the art, there is clearly some benefit in having access to a biocatalyst with an alternative specificity to those more usually used. As demonstrated in Example 8, the esterase described by the present invention not only has good stereo-specific activity, but also has shown an opposite specificity to a large range of commercially-available enzyme preparations.

The invention has been described in terms of the use of a non-immobilised biocatalyst catalysing hydrolytic reactions. However, in carrying out biotransformations using hydrolytic enzymes, such as the esterase described herein, a number of alternative methodologies are well known to those skilled in the art. Thus, it is now well established that some economic advantage may sometimes be gained by immobilising the enzyme, in any number of ways, thus facilitating enzyme recovery, reuse and, in some instances, stability. Likewise under reaction conditions of lower water activity, it is possible to use such biocatalysts to carry out synthetic, transesterification or interesterification reactions. Such considerations are a matter for conventional process development and optimisation.

The following Examples illustrate the invention.

EXAMPLE 1

The following medium was used for the growth of the organism:

| | |
|---|---|
| $(NH_4)_2SO_4$ (g/l) | 0.5 |
| $MgSO_4.7H_2O$ (g/l) | 0.25 |
| $CaCl_2.2H_2O$ (g/l) | 0.1 |
| $KH_2PO_4$ (g/l) | 8.0 |
| Yeast Extract (g/l) | 10.0 |
| Glucose (g/l) | 5.0 |
| Trace element solution (µl/l) | 100 |
| pH (with NaOH) | 6.5 |
| The trace element solution used was: | |
| $CaCl_2.2H_2O$ (g/l) | 3.57 |
| ZnO (g/l) | 2.0 |
| $CuCl_2.2H_2O$ (g/l) | 0.85 |
| $Na_2MoO_4.2H_2O$ (g/l) | 4.8 |
| $MnCl_2.4H_2O$ (g/l) | 2.0 |
| $FeCl_3.6H_2O$ (g/l) | 5.4 |
| $H_3BO_4$ (g/l) | 0.3 |
| $CoCl_2.6H_2O$ (g/l) | 2.4 |
| HCl (ml/l) | 250 |

Cells of AJ3 were inoculated into 100 ml medium in a 1 liter shake flask. This culture was grown with shaking at 30° C. for 48 hours. 10 ml was then transferred into 90 ml fresh medium in a 1 liter shake flask and grown for a further 8 hours at 30° C. with shaking. This flask was used to inoculate a 2.8 l laboratory fermenter with 1.5 l medium plus 5 g/l glucose and 0.5 ml/l of a silicone/PPG-based antifoam (XF0371, Ivanhoe Chemicals, Ill., U.S.A.). This fermenter was operated for 48 hours with agitation and aeration, controlled to maintain a DOT >50% air saturation and temperature and pH at 30° C. and 6.0 respectively.

At the completion of the fermentation the cells were harvested by centrifugation and the pellet resuspended at 10% w/v (based on wet cell weight) in lysis buffer, i.e. 0.1M sodium carbonate in 5% Triton X-100 aqueous solution. Lysis was carried out overnight at 8° C. with shaking after which the enzyme activity-containing lysate was separated from the cell debris by centrifugation. The lysate was then diluted 50% in lysis buffer, prior to its being used to carry out resolution.

Racemic ethyl naproxen (ethyl 6-methoxy-α-methyl-2-naphthaleneacetate) was dissolved in cyclohexane to a concentration of 19 mg/ml. 2 ml of this solution was then mixed with 5 ml of prepared crude enzyme solution in a glass vial and reacted with shaking for 72 hours at 23° C.

Analysis of the aqueous phase of the reaction mixture after 72 hours showed accumulation of naproxen to 2.76 mg/ml, equivalent to about 40% conversion. HPLC analysis of the enantiomeric purity of this naproxen showed it to have an ee (enantiomeric excess) of 93% in favour of the (S) enantiomer (equivalent to 96.5% pure).

EXAMPLE 2

Cells of AJ3 were inoculated from a malt extract agar plate into 30 ml growth medium in a 250 ml baffled flask. This was shaken for 30 hours at 23° C. and then 2.5 ml transferred into a second 250 ml baffled flask containing 30 ml of the same medium as in Example 1. Following growth for 40 hours, at 23° C. with shaking, racemic ethyl ketoprofen was added to the broth to a concentration of 20 g/l. The biotransformation was then allowed to proceed for 120 hours, after which HPLC analysis showed there to have been 18.2% hydrolysis of the added ester. The enantiomeric excess of the ketoprofen acid formed was found to be 96% in favour of the (S)- enantiomer.

EXAMPLE 3

A crude enzyme solution was prepared, using the same growth medium as in Example 1, minus glucose and at a pH of 6.0. Cells of AJ3 were inoculated into 100 ml medium in a 1 liter shake flask. This culture was grown with shaking at 30° C. for 48 hours. 10 ml was then transferred into 90 ml fresh medium in a 1 liter shake flask and grown for a further 8 hours at 30° C. with shaking. This flask was used to inoculate a 2.8 l laboratory fermenter with 1.5 l medium plus 5 g/l glucose and 0.5 ml/l of a silicone/PPG-based antifoam (XF0371, Ivanhoe Chemicals, Ill., U.S.A.). This fermenter was operated for 48 hours with agitation and aeration, controlled to maintain a DOT >50% air saturation and temperature and pH at 30° C. and 6.0 respectively.

At the completion of the fermentation the cells were harvested by centrifugation and the pellet resuspended at 10% w/v (based on wet cell weight) in lysis buffer, i.e. 0.1M sodium carbonate in 5% Triton X-100 aqueous solution. Lysis was carried out overnight at 8° C. with shaking after which the enzyme activity-containing lysate was separated from the cell debris by centrifugation.

Racemic ethyl ketoprofen was dissolved in each of four organic solvents: toluene, cyclohexane, methanol and MTBE (methyl t-butyl ether) to a concentration of 20 g/1.2 ml of each of these solutions was added to 5 ml aliquots of crude enzyme solution in glass vials. A control aqueous biotransformation containing 5 ml crude enzyme solution, 400 μl 50% racemic ethyl ketoprofen, 0.5% w/v Tween 80 stock solution and 2.5 % w/v Triton x-100 was also prepared in a glass vial. All samples were reacted with shaking for 48 hours at 25° C. Analysis of the aqueous phase of each reaction mixture gave the results shown in Table 1.

TABLE 1

HYDROLYSIS OF RACEMIC ETHYL KETOPROFEN IN 2-PHASE BIOTRANSFORMATIONS

| SAMPLE SOLVENT | ACID PRODUCED (mg · ml$^{-1}$) | CONVERSION (%) |
|---|---|---|
| AQUEOUS | 2.3 | 6.2 |
| TOLUENE | 0.1 | 1.3 |
| CYCLOHEXANE | 1.1 | 14.1 |
| METHANOL | 0.4 | 4.6 |
| MTBE | 0.7 | 8.3 |

It is observed that the biotransformation works to a certain extent in the presence of cyclohexane or MTBE as solvents, but is quite strongly inhibited by toluene under these conditions.

EXAMPLE 4

Various esters of racemic ketoprofen were dissolved in cyclohexane to a concentration of 20 g/l. The esters used were methyl, ethyl, n-propyl, n-butyl, n-pentyl, n-hexyl. In the case of methyl ester, a suspension was prepared due to low solubility of ester in cyclohexane.

To 5 ml aliquots of crude enzyme solution in glass vials was added 2 ml of each of the six racemic ketoprofen ester solutions above. An aqueous control biotransformation was also prepared in a glass vial containing 5 ml crude enzyme solution, 200 μl 50% racemic ethyl ketoprofen,0.5% Tween 80 stock solution and 2.5% w/v Triton x-100. Reactions were conducted with shaking for 24 hours at 25° C. HPLC analysis of the aqueous phase of each biotransformation gave the results shown in Table 2.

TABLE 2

HYDROLYSIS OF RACEMIC KETOPROFEN ESTERS IN 2 PHASE BIOTRANSFORMATIONS

| KETOPROPEN ESTER | ACID PRODUCED (mg · ml$^{-1}$) | CONVERSION (%) | EE (%)(S)-enantiomer |
|---|---|---|---|
| AQUEOUS CONTROL | 4.6 | 22.9 | 90 |
| METHYL | 1.7 | 42.3 | 90 |
| ETHYL | 1.1 | 27.5 | 100 |
| n-PROPYL | 1.0 | 25.6 | 86 |
| n-BUTYL | 0.3 | 8.0 | N/D |
| n-PENTYL | 0.18 | 4.4 | N/D |
| n-HEXYL | 0.09 | 2.3 | N/D |

N/D = not determined owing to the low acid accumulated.

EXAMPLE 5

The AJ3 isolate was grown to the 500 liter scale using the following methodology.

AJ3 was inoculated into 100 ml medium (as Example 1) in a 1 liter point baffled flask. Following growth for 48 hours at 25° C. with orbital shaking (300 rpm, 25 mm throw), 1 ml was transferred to each of three 1 liter baffled flasks each containing 100 ml medium. The cultures were then grown for a further 48 hours under similar conditions before being combined and used to inoculate a 750 l fermenter containing 500 l medium.

| MgSO$_4$.7H$_2$O | 0.4 g/l |
|---|---|
| CaCl$_2$.2H$_2$O | 0.1 g/l |
| KH$_2$PO$_4$ | 8.0 g/l |
| Yeast Extract | 30.0 g/l |
| Trace Element Solution | 200 μl/l (as Example 1) |
| Antifoam (XFO-371) | 0.5 ml/l |
| pH (with NaOH) | 6.0 |

This medium was sterilised at 121° C. for 50 minutes prior to the addition of 15 l of 50% w/v sterile glucose solution.

Control conditions were: temperature 25° C., pH at 6.0 phosphoric acid or sodium hydroxide addition and DOT ≧50% of air saturation by agitation and aeration control.

After 64 hours growth, cells were treated in situ to kill them and to aid lysis. This was done by dropping the temperature to 15° C. and adding sodium hydroxide to bring the pH to 10. After 50 minutes' treatment, the broth was readjusted to pH 7 with phosphoric acid and the cells harvested in a continuous centrifuge. The collected cells were distributed into different containers and stored at −20° C. until required.

Frozen cells were thawed and resuspended at 25% w/v (based on wet cell weight) in 50 mM KH$_2$PO$_4$, pH 6.5. After stirring for 30 minutes, the cells were collected by centrifugation. Cells were then resuspended at 25% w/v (based upon wet cell weight) in lysis buffer, i.e. 0.3M Na$_2$CO$_3$, pH 10.5. Lysis was conducted overnight at 4° C. with stirring, after which the lysate was clarified by centrifugation to separate cell debris from the supernatant. The enzyme solution (i.e. lysate supernatant) was assayed for activity using standard biotransformation conditions, i.e. 1 ml enzyme solution suitably diluted in 0.1M Na$_2$CO$_3$, pH 10.0, 40 μ 50% racemic ethyl ketoprofen, 0–5% Tween 80 stock solution, 2.5. w/v Triton X-100. Biotransformations were carried out in a sealed 20 ml volume glass vial with shaking for 1 hour at 25° C. Activity is expressed as U/ml activity where 1 unit (U)=1 mg ketoprofen acid produced per hour at 25° C. Enzyme solutions were considered suitably diluted if the assayed activity was in the range of 1 to 5 U/ml.

A 50% racemic ethyl ketoprofen stock solution was prepared as follows: 25 g racemic ethyl ketoprofen and 0.25 g Tween 80 were added to 10 ml distilled water and this mixture sonicated for 5 mins (15 amplitude μm, 10 seconds on/10 seconds off cycle). The volume was then made up to 50 ml with distilled water, and the stock solution autoclaved to sterilise and allow for longer term storage.

A typical lysate activity was 1.5 U/ml.

EXAMPLE 6

Clarified lysate (Example 5) was diafiltered against distilled water (Amicon DC2 ultra-filtration unit using 30,000 molecular weight cut off hollow fibre cartridges) until the conductivity of the lysate reached that of 20 mM $Na_2CO_3$, pH 9.2 buffer (Buffer A). The solution was then concentrated 4–5 fold and typically retained >90% initial activity. Enzyme activity was loaded batchwise onto pre-equilibrated QA52 anion exchange resin (Pharmacia) for 1 hour at ambient temperature, at a loading of 7–10 U of activity per ml of wet QA52 gel. The loaded gel was packed into a column at a linear flow rate of 200 mm/h. Chromatography was subsequently conducted at 40° C.

The column was washed to baseline with Buffer A. Elution was performed using a 10 column volume gradient of 0–05M NaCl in Buffer A and fractions corresponding to 1/35 gradient volume were collected. The elution profile typically obtained is shown in Table 3.

TABLE 3

ELUTION PROFILE FOR 1ST PASS QA52 CHROMATOGRAPHY

| FRACTION | TOTAL ACTIVITY (U.) | RECOVERY (%) |
|---|---|---|
| LOAD | 99 | — |
| FLOW THROUGH | 0 | 0 |
| WASH | 0 | 0 |
| 1 | 0 | 0 |
| 5 | 0.3 | 0.3 |
| 6 | 2.0 | 2.0 |
| 7 | 6.6 | 6.7 |
| 8 | 19.5 | 19.7 |
| 9 | 22.2 | 22.4 |
| 10 | 10.0 | 10.1 |
| 11 | 2.5 | 2.5 |
| 13 | 1.0 | 1.0 |
| 17 | 0.3 | 0.3 |

Activity was eluted in the NaCl concentration range of 0.12–0.18M. Fractions 7–10 were inclusively to give:

fraction activity recovery=63.5% fraction protein recovery=15.8% The pooled activity was concentrated using a YM 30 membrane in a stirred cell ultrafiltration AMICON) with no loss of activity, and dialysed against Buffer A until a conductivity 3.2–3.6 mS was attained. This was then re-chromatographed on QA52 resin with the results in Table 4.

TABLE 4

ELUTION PROFILE FOR 2ND PASS QA52 CHROMATOGRAPHY

| FRACTION | TOTAL ACTIVITY (U.) | RECOVERY (%) |
|---|---|---|
| LOAD | 3111 | — |
| FLOW THROUGH | 0 | 0 |
| WASH | 0 | 0 |
| 13 | 60 | 1.9 |
| 14 | 193 | 6.2 |
| 15 | 407 | 13.1 |
| 16 | 828 | 26.6 |
| 17 | 890 | 28.6 |
| 18 | 445 | 14.3 |
| 19 | 152 | 4.9 |
| 20 | 81 | 2.6 |

In this second pass, activity was eluted in the NaCl concentration range of 0.2–0.25M NaCl. Fractions 15–17 were pooled inclusively. The cooled sample was assayed for activity and protein content.

Activity=27.8 U. $ml^{-1}$

Total activity=2599 U

Total activity recovery 83.5%

Protein (biuret method)=1.34 $mg.ml^{-1}$

Total protein=125 mg

Total protein recovery=5.5%

The pooled fractions were further purified using a Pharmacia MONO P HR 5/5 pre-packed anion exchange FPLC. The chromatographic conditions were as follows;

Low salt buffer=20 mM Ethanolamine-HCl pH 9.0

High salt buffer=20 mM Ethanolamine-HCL+0.3M NaCl pH 9.0

Flow rate=1 ml/min.

| Gradient profile | |
|---|---|
| Time | NaCl concentration |
| 0–5 mins | 0 M |
| 5–7 mins | 0–0.1 M |
| 7–20 mins | 0.1–0.3 M |
| 20–22 mins | 0.3 M |
| 22–23 mins | 0.3–0 M |
| 23–25 mins | 0 M |

Sample volume=1 ml

Fraction volume=1 ml

The pooled fractions from the 2nd pass QA52 chromatography were concentrated 10 fold through a 30,000 molecular weight cut off ultrafiltration membrane and the resulting concentrate desalted into low salt buffer for HPLC, using a Pharmacia G-25 PD10 gel filtration column. Approximately 5 mg total protein were loaded onto the HPLC column per run. The following elution profile was obtained (Table 5):

TABLE 5

ELUTION PROFILE FROM MONO P ANION EXCHANGE HPLC

| FRACTION (mins) | ACTIVITY (U · $ml^{-1}$) | RECOVERY (%) |
|---|---|---|
| LOAD | 104.0 | — |
| 8 | 5.7 | 5.5 |
| 9 | 63.8 | 61.3 |

TABLE 5-continued

ELUTION PROFILE FROM MONO P ANION EXCHANGE HPLC

| FRACTION (mins) | ACTIVITY (U · ml$^{-1}$) | RECOVERY (%) |
|---|---|---|
| 10 | 28.3 | 27.2 |
| 11 | 7.5 | 7.2 |
| 12 | 1.9 | 1.8 |
| 13 | 0.0 | 0.0 |

Fractions 9 and 10 were pooled to give a total recovery of 88.5%. This pooled activity was then further purified by size exclusion HPLC.

An Analgel-TSK G3000 SWXL 30 cm×7.8 mm size exclusion HPLC column was used for the following separation. The following chromatographic conditions were employed:

Buffer–0.1M $K_2HPO_4$ +20 mM $Na_2EDTA$ pH 7.0
Flow rate=0.4 ml.min$^{-1}$
Sample volume=200 μl
Fraction volume=400 μl The pooled fractions from the MONO P ion exchange HPLC were concentrated 1.5 fold through a 10,000 molecular weight cut off ultrafiltration membrane The concentrated sample was desalted into size exclusion HPLC buffer using a Pharmacia G25 pd10 column. The following elution profile was obtained (Table 6).

TABLE 6

ELUTION PROFILE FROM SIZE EXCLUSION HPLC

| FRACTION (mins) | ACTIVITY (U · ml$^{-1}$) | RECOVERY (%) |
|---|---|---|
| LOAD | 131.0 | — |
| 17.5 | 0.0 | 0 |
| 18.5 | 0.0 | 0 |
| 19.5 | 1.5 | 2.3 |
| 20.5 | 13.3 | 20.3 |
| 21.5 | 7.5 | 11.5 |
| 22.5 | 2.6 | 4.0 |
| 23.5 | 0.8 | 1.2 |

An estimation of the molecular weight of our AJ3 racemic ethyl ketoprofen esterase was made by SDS-PAGE (sodium dodecyl sulphate Polyacrylamide Gel Electrophoresis). A pre-cast 12% homogeneous SDS-PAGE mini-gel (BDH) was run using prestained molecular weight protein standard markers (BISC) for molecular weight comparison. The running Buffer was Electrograd Buffer TTS (BDH). Electrophoresis was carried out at a constant voltage (200 V) and limiting current (40 mA per gel) until the blue dye front had passed completely through the gel. Protein was visualised by Coomassie Blue staining.

The band of protein corresponding to the esterase was identified by comparison of protein banding in active and non-active samples. Comparison of the relative migration distances of the active protein and the protein standards indicated the novel purified denatured protein had a molecular weight slightly greater than the 32,500 Da marker.

The pH profile of the biotransformation was tested using the pooled material described above, following 4 months storage at −20° C. An aliquot was thawed at ambient temperature, and diluted 10-fold with distilled water (diluted enzyme solution). 1.1M buffer stock solutions were prepared at the following pH, using the salts indicated (pH was adjusted as necessary using sodium hydroxide or hydrochloric acid):

| pH 6.0 | $NaH_2PO_4$ |
| pH 7.0 | $NaH_2PO_4$ |
| pH 8.0 | $NaH_2PO_4$ |
| pH 9.0 | Glycine-HCl |
| pH 10.0 | Glycine-HCl |
| pH 11.0 | $Na_2HPO_4$ |

The biotransformation reactions were set up in sealed glass vials as follows:

1 ml diluted enzyme solution
100 μl relevant 1.1M pH buffer stock solution
40 μl 50% racemic ethyl stock solution
2.5% w/v Triton X-100

For a biotransformation at pH 12.0, 1M NaOH solution was added directly to a pH 11.0 reaction mixture until the correct pH was reached. All biotransformations were set up in duplicate and reactions were carried out for 1 hour with shaking at 25° C. The main results of the reactions are shown in Table 7. Maximum activity was found at pH 10.

TABLE 7

AJ3 BIOTRANSFORMATION pH PROFILE

| BIOTRANSFORMATION pH | ACTIVITY (U · ml$^{-1}$) | NORMALISED RECOVERY (%) |
|---|---|---|
| 6 | 1.32 | 27.6 |
| 7 | 1.97 | 41.2 |
| 8 | 2.47 | 51.7 |
| 9 | 2.95 | 61.7 |
| 10 | 4.78 | 100.0 |
| 11 | 2.35 | 49.2 |
| 12 | 0.36 | 7.5 |

EXAMPLE 7

This Example illustrates the cloning of the stereo-specific esterase from the isolate AJ3, and the use of the product.

Isolation of poly(A)+m-RNA 10 g of filtered AJ3 mycelium was ground under liquid nitrogen into a fine powder. The total genomic RNA was then isolated from the ground mycelium using the acid guanidinium thiocyanate-phenol-chloroform extraction method as detailed by Chomczynski & Sacchi, Anal. Biochem. 162:156–159 (1987). This method yielded 8.76 mg/ml of total genomic RNA with a 260:280 nm ratio of 1.704.

The poly(A)$_+$ m-RNA was isolated from the total genomic RNA by affinity chromatography on oligo (dT)-cellulose as detailed by Sambrook et al in Molecular Cloning, A Laboratory Manual, 2nd Ed., Cold Spring Harbor Laboratory Press (1989). Specifically, 0.5 g of oligo (dT)-cellulose was resuspended in 10 ml of 0.1M NaOH, and 1 ml of this slurry was poured into a 2.5 ml sterile disposable syringe barrel. A packed bed volume of 0.8 ml was achieved. 10.5 mg of total genomic RNA was allowed to bind to the equilibrated oligo (dT)-cellulose. The genomic RNA was eluted from the column using excess volumes of column loading buffer. Progress was monitored spectrophotometrically, the eluate being analysed at 260 nm. When there was no appreciable absorbance at 260 nm, the poly(A)$^+$ m-RNA was eluted using a suitable elution buffer. Progress was monitored spectrophotometrically. The samples were pooled and then reapplied to the oligo (dT)-cellulose, and the elution effected again. The final samples yielded 85 μg/ml of high purity poly(A)$^{30}$ m-RNA.

Preparation of a c-DNA library

The c-DNA library was constructed using the ZAP-cDNA synthesis kit (Stratagene Ltd., La Jolla, Calif., U.S.A.). 8.5 µg of the poly(A)+ m-RNA were used at the onset of the protocol. The efficacies of the first and second syntheses were analysed by autoradiogeaphy. Following spin column gel filtration chromatography through Sephacryl S-400, the size-fractionated c-DNA samples were quantified using ethidium bromide-impregnated agarose; values in excess of 10 ng/µl were measured. High molecular weight c-DNA samples were ligated into the uni-ZAP XR vector, and then packaged into $E.$ $coli$ XL1-Blue MRF' using the Gigapack II packaging extracts (Stratagene Ltd.). The titre of the resultant c-DNA library was $1.63 \times 10^{10}$ plaque-forming units (pfu)/ml.

Screening of the c-DNA library for esterase activity

Sufficient recombinant phage were used, to yield 50,000 pfu against $E.$ $coli$ XL1-Blue MRF' when cultivated on 150 mm NZY agar plates. $1.2 \times 10^6$ recombinant phage were allowed to develop under inducing conditions (i.e. in the presence of 2.5 mM IPTG). The phage were screened for esterase activity using a 0.1% w/v S(+) ketoprofen ethyl ester agarose overlay. Esterase activity was indicated by conversion of the poorly water soluble ethyl ester to soluble ketoprofen acid. After an overnight incubation at 24° C., 8 discrete clearance zones were noted. The plaques associated with the clearance zones were cored and the phage recovered. The esterase-positive phage were reamplified in $E.$ $coli$ XL1-Blue MRF', retitred and screened for esterase activity, using both the substrate overlay method and by HPLC.

In vivo excision of the recombinant p-Bluescript from Uni-ZAP-XR

The recombinant p-Bluescript phagemid located within the Uni-ZAP XR vector was excised from the vector using the ExAssist/SOLR system (Stratagene Ltd.). 62 recombinant phagemids were rescued and inherited stably in $E.$ $coli$ SOLR. All of these recombinant $E.$ $coli$ were screened for esterase activity using the substrate overlay method and proved to be positive. A comparison of colony diameter versus substrate clearance zone diameter indicated that strain numbers 47 and 62 were worthy of further study, and were designated CS47 and CS62, respectively.

Restriction digest map of recombinant plasmids 400 ml LB plus ampicillin (50 µg/ml) cultures of recombinant $E.$ $coli$ XL1-Blue MRF' strains CS47 and CS62 were grown. Plasmids (designated pCS47 and pCS62, respectively) were prepared from them by the method of Holmes & Quigley (Anal. Biochem. 114:193 (1981)), and purified by ultracentrifugation in CsCl-ethidium bromide gradients. These were then subjected to a number of restriction endonuclease digestions, using commercially-available enzymes and under the suppliers conditions. Fragment sizes were assessed by agarose gel electrophoresis, different percentages of agarose being used to confirm fragment sizes. Results of the restriction digest are shown in FIG. 1. Notably, pCS47 was approximately 200 base pairs shorter than pCS62 at the 5' end.

Growth of recombinant strain

Recombinant strain CS62 was inoculated into 100 ml LB medium plus 50 µg/ml ampicillin in a 1 liter shake flask. This was incubated for 15 hours at 37° C. with shaking (orbital shaker, 25 mm throw) at 300 rpm. This was then inoculated at 1% into 1.5 liter medium in a 2.8 liter laboratory fermenter. The following medium was used:

| | |
|---|---|
| Tryptone (Unipath Ltd., Hants., UK) | 12.0 g/l |
| Yeast extract (Unipath Ltd.) | 24.0 g/l |
| Glycerol | 4.0 ml/l |
| $KH_2PO_4$ | 2.3 g/l |
| $K_2HPO_4 \cdot 3H_2O$ | 16.4 g/l |

The temperature was maintained at 25° C., the pH at 7.0 by automatic addition of 10% phosphoric acid as required, and the dissolved oxygen tension >50% of air saturated by agitation control. An air flow rate of 0.75 1/min was used. Growth was monitored by measurement of sample absorbances at 520 nm against a medium blank after suitable dilutions. At an absorbance of 0.9, IPTG (isopropyl-β-D-thiogalactoside) was added to a final concentration of 240 µg/ml.

After 24 hours growth in the fermenter, the cells were harvested by centrifugation and stored at −20° C. until required.

Use of recombinant strain

Cells of CS62 grown and stored as described above were used to provide enzyme for use in the hydrolysis of ethyl naproxen. Cells were resuspended at 10% w/v in 0.1M sodium carbonate, pH 10, and lysed by sonication for 10 minutes (10 seconds on, 10 seconds off cycles) at 4° C. The enzyme lysate was then centrifuged to obtain a cell-free supernatant solution.

Racemic ethyl naproxen was dissolved in cyclohexane to a concentration of 100 g/l. 200 µl of this solution was added to 1 ml enzyme solution and shaken for 1 hour at 25° C. The phases were then separated and the aqueous phase analysed (by reverse phase HPLC) for naproxen accumulation. It was found that naproxen had accumulated to 5.3 g/l (about 26% conversion). Analysis showed an ee of >95% in favour of the S-enantiomer (the (R)-enantiomer was so low that it could not reliably be measured).

Analysis of a biotransformation using an enzyme extract from $E.$ $coli$ SOLR (the host non-recombinant strain) showed no activity against the ester.

EXAMPLE 8

Cells (grown as per Example 7) were resuspended at 5% w/v in 100 mM TRIS, pH 8, and lysed by sonication for 15 minutes (10 seconds on, 10 seconds off cycle) at an amplitude of 20 µm in a Soniprep 150. The lysate was centrifuged to remove cell debris and the supernatant used in biotransformation.

10 g of the racemic butyrate ester of 2-methoxycyclohexanol was mixed with 100 ml of 100 mm TRIS, pH 8, by magnetic stirring. 20 ml of the above lysate of CS62 was added. The temperature of the biotransformation was controlled at 25° C. and the pH at 8.0 by the addition of 1M NaOH. Samples were removed and monitored for 2-methoxycyclohexanol formation. NaCl was added to saturation to 1 ml sample which was then extracted into 1 ×5 volumes of toluene. The toluene layer was removed and dried by the addition of $MgSO_4$. The sample was then analysed by GC. A 15 m DB-5 column with 0.25 µm film was used with helium as the carrier, at 55.2 kPa, the oven temperature was 60° C. for 1 minute, raised at 10° C./min to 150° C., and this temperature was then held for a further minute.

The ee of the 2-methoxycyclohexanol formed was determined following derivatisation with trifluoroacetic anhydride (TFAA). 20 µl of TFAA was added to 1 ml of the toluene-extracted sample which was then allowed to stand at ambient temperature for 30 minutes. The diastereomers were resolved by GC using a 30 m GTA column (Chiraldex) at 96 kPa, helium as carrier gas and with the oven at 110° C.

After 41 hours reaction, there was 44% conversion of the substrate, with an ee of the 2-methoxycyclohexanol of 96% in favour of the (S)-enantiomer.

The stereo-specific activity of this biocatalyst is considered unusual. A screen of 12 commercially-available lipase/esterase preparations on the above substrate showed none which had this specificity, for the (S)-enantiomer. Thus, commercially-available lipase/esterase preparations from porcine pancreatic lipase, *Rhizopus arrhizius, Rhizopus delemar, Mucor miehei, Aspergillus niger, Penicillium cyclopium, Pseudomonas fluorescens* all showed specificity for the (R)-enantiomer, whereas preparations from *Candida cylindracae, Mucor javanicus* and cholesterol esterase showed no specificity. Other preparations from *Penicillin roquefortii* and *Candida lipolytica* showed minimal if any activity against the racemic butyrate ester of 2-methoxycyclohexanol. Therefore, none of the above shows high specificity for hydrolysis of the (S)-enantiomer. This is potentially advantageous in that it enables access to the (S)-enantiomer as the alcohol without having to exceed 50% conversion.

What we claim is:

1. A method for preparing an enantiomerically-enriched chiral compound, comprising:

treating a mixture of enantiomers of a carboxylic acid ester with a composition selected from the group consisting of an organism of the genus Ophiostoma or Ceratocystis and an esterase derived from an organism of the genus Ophiostoma or Ceratocystis, whereby one enantiomer of said ester is selectively hydrolyzed to form an enantiomerically-enriched carboxylic acid or alcohol, and the remaining unhydrolyzed ester is enantiomerically-enriched.

2. The method of claim 1, wherein said organism has the ability to react stereo-selectively with racemic ethyl naproxen and give (S)-naproxen in at least 93% enantiomeric excess, at 15–25% conversion.

3. The method of claim 1, wherein said organism has the ability to react stereo-selectively with racemic ethyl ketoprofen and give (S)-ketoprofen in at least 93% enantiomeric excess, at 15–25% conversion.

4. The method of claim 1, wherein said organism is *Ophiostoma novo-ulmi*, IMI 356050.

5. The method of claim 1, wherein said mixture of enantiomers is racemic.

6. The method of claim 1, wherein said ester is a $C_{1-3}$ alkyl ester of a chiral 2-arylalkanoic acid.

7. The method of claim 1, wherein the carboxylic acid is naproxen.

8. The method of claim 5, wherein said mixture is racemic ethyl naproxen and the product of hydrolysis is (S)-naproxen.

9. The method of claim 1, wherein the carboxylic acid is ketoprofen.

10. The method of claim 9, wherein said mixture is racemic ethyl ketoprofen and the product of hydrolysis is (S)-ketoprofen.

11. The method of claim 1, wherein the alcohol is chiral.

12. The method of claim 1, wherein the hydrolysis is conducted at pH 8 to 11.

13. The method of claim 12, wherein the hydrolysis is conducted at pH 9.5 to 10.5.

14. A method for preparing an enantiomerically-enriched chiral compound, comprising:

treating a mixture of enantiomers of a carboxylic acid ester with a composition selected from the group consisting of an organism of the genus Ophiostoma or Ceratocystis and an esterase derived from an organism of the genus Ophiostoma or Ceratocystis, whereby one enantiomer of said ester is selectively hydrolyzed to form a substantially enantiomerically-enriched carboxylic acid or alcohol, and the remaining unhydrolyzed ester is substantially enantiomerically-enriched.

* * * * *